United States Patent [19]

Gainer

[11] 4,038,144

[45] July 26, 1977

[54] METHOD OF INCREASING FERMENTATION YIELDS

[75] Inventor: John L. Gainer, Charlottesville, Va.

[73] Assignee: The University of Virginia, Charlottesville, Va.

[21] Appl. No.: 678,113

[22] Filed: Apr. 19, 1976

[51] Int. Cl.² .......................... C12B 3/12; C12D 1/00; C12B 1/00
[52] U.S. Cl. .................................. 195/100; 195/114; 195/80 R; 195/81; 195/96
[58] Field of Search .......................... 195/114, 99–103, 195/27

[56] References Cited

U.S. PATENT DOCUMENTS 3,788,468  1/1974  Gainer .................................. 210/59

*Primary Examiner*—Lionel M. Shapiro
*Attorney, Agent, or Firm*—Oblon, Fisher, Spivak, McClelland & Maier

[57] ABSTRACT

A method of increasing the yield of a fermentation process comprises adding a water-soluble carotenoid to the nutrient medium.

9 Claims, No Drawings

METHOD OF INCREASING FERMENTATION YIELDS

BACKGROUND OF THE INVENTION

1. Field of the Invention

This invention relates to fermentation processes in general. More particularly, it relates to a method for increasing the yields of fermentation processes.

2. Description of the Prior Art

In applicant's prior applications, now U.S. Pat. Nos. 3,853,993, 3,788,468, 3,965,261 and 3,975,519 and Ser. No. 608,400, filed Aug. 27, 1975, Ser. No. 630,684, filed Nov. 10, 1975, Ser. No. 634,149, filed Nov. 11, 1975, now allowed and Ser. No. 678,551, filed Apr. 20, 1976, applicant has disclosed that certain water-soluble carotenoids have been observed to possess quite unique properties.

Applicant has continued to study the unique properties of this unique class of compounds with the result that a new property related to fermentation processes has been discovered.

In many industrial fermentation processes, the ultimate limitation on the growth of the cells is the rate at which nutrients can be supplied to the microbes. These nutrients include not only the substrate on which the microbes grow, but also, in some cases, dissolved gases such as oxygen. Supplying these materials to the microorganisms through the media in which they are growing is basically a problem in diffusional mass transfer.

In the past, extensive research has centered on ways to minimize diffusional resistances to mass transfer. This has been done primarily by optimizing agitation in order to both achieve high ratios of interfacial area to volume and to reduce diffusional film resistances. However, methods designed to improve the molecular diffusivities of the nutrients in the media to the growing cells have been ignored. Applicant has now performed experiments designed to determine the effect of water-soluble carotenoids in this area.

SUMMARY OF THE INVENTION

As a result, it has now been found that the water-soluble carotenoids, such as crocetin and crocin, can be used effectively to increase the yield of fermentation-produced chemicals and pharmaceuticals.

DETAILED DESCRIPTION OF THE PREFERRED EMBODIMENTS

The mechanism by which the water-soluble carotenoids increase fermentation yields is not clear. However, the following speculative theoretical mechanism which is meant in no way to limit this invention, is believed to be involved.

Many nutrients can be supplied to solutions in sufficient strength so that the principal limitations on their use by the cells are the rates of the biological functions of the microorganism involved. Such is not always the case with such nutrients or gases, though. For example, gaseous oxygen is sparingly soluble in liquid media. Therefore, it must be continuously supplied to the fermentor as it is used. Another consequence of this low solubility is believed to be the limit it imposes on the rate of oxygen supply to the culture broth. Because of its low solubility, no large driving force for oxygen can ever develop, and even the maximum supply rate under normal conditions is rather low. So, although the rate of transport of any nutrient to the growing microorganism is important in determining the amount of growth of the organism, the rate of transport of oxygen is of particular importance. It is believed that at least part of the effect of the water-soluble carotenoids is to increase the rate of diffusion of all species, including oxygen, in the nutrient medium, thereby increasing the rate of supply to the growing cells. Such an increase in supply of nutrients and respiratory gases may well result in increased yields, or growth of the microbial cells. Since many chemicals and pharmaceuticals can be produced via fermentation methods, the increasing of diffusivity will mean increased production of these compounds.

In any event, the carotenoids useful for this purpose are those which are water-soluble. Preferred are those of the form:

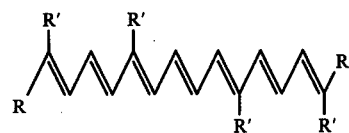

wherein each R may represent a hydrophilic group and each R' represents hydrogen or methyl. Suitable hydrophilic groups include the carboxyl groups or the ester groups of the form COOR'' wherein R'' represents a soluble sugar group, such as $C_{12}H_{21}O_{10}$, an alkanol group, such as —$CH_2$—OH, —$CH_2$—$CH_2$—OH, or —$CH_2$—$CH_2$—$CH_2$—OH, or a carboxyl substituted lower alkyl, such as —$CH_2$—COOH, —$CH_2$—$CH_2$—COOH or —$CH_2$—$CH_2$—$CH_2$COOH, or each R and R' may represent a lower alkanol group, such as —$CH_2$—OH, —$CH_2$—$CH_2$—OH, or —$CH_2$—$CH_2$—$CH_2$—OH, a hydroxy group, or an amine group of the form —NH or NR''' wherein R''' is a lower alkyl, lower alkanol or carboxy substituted lower alkyl, or a carboxy substituted lower alkyl, such as —$CH_2$—$CH_2$—COOH, —$CH_2$—COOH, —$CH_2$—$CH_2$—$CH_2$COOH.

Most preferred are crocetin, also known as 8,8'-diapo-8,8'-carotenoic acid, or crocin, also known as digentiobiosyl 8,8'-diapo-8,8'-carotenedioate, or a salt, such as the sodium salt, of crocetin.

Although the carotenoids have been identified herein as "water soluble carotenoids", it should be understood that they are also soluble in hydrocarbons due to their long chain hydrocarbon structure.

The water-soluble carotenoids of this invention are useful in increasing the yield of any fermentable species whose rate of production is limited by nutrient supply rates. Typical of such fermentation produced chemicals are: antibiotics, vitamins, enzymes, proteins, glucose, acids, alcohols, ammonia, hydrocarbons and other chemicals and pharmaceuticals. They are also useful in increasing the rate of destruction of materials by fermentation such as in treatment of sewage sludges.

The water soluble carotenoid should be added at the beginning of the fermentation process, and also intermittently until the fermentation is stopped. The amount to be added is dependent upon whether or not the water-soluble carotenoid is also metabolized by the microbes and upon the amounts of other compounds present in the fermentation media. Amounts in the range of from 0.1 mg/liter of broth to 1000 mg/liter of broth are generally suitable. The preferred concentration range is from 1 mg/liter to 50 mg/liter of broth, especially for the sodium salt of crocetin.

The most beneficial effects on yield are effected when this invention is used in conjunction with fermentation media having higher protein concentrations, but the presence of protein in the media is not necessary for the water-soluble carotenoids to increase yields.

The water-soluble carotenoids are preferably added in the following manner. The carotenoid, such as crocetin, is first dissolved in sodium hydroxide. Hydrochloric acid is added until the pH of the solution is between 7.5 and 8.0. Such a procedure sterilizes the carotenoid before it is added to a fermentation broth. When the carotenoid is heat sensitive, e.g., for crocetin, it should not be autoclaved or steam sterilized. However the carotenoids such as crocetin will remain active at the temperatures usually used in fermentation processes. Many carotenoids such as crocetin are also light-sensitive, and should be kept from exposure to light as much as possible.

Having generally described the invention, a more complete understanding can be obtained by reference to certain specific examples, which are included for purposes of illustration only and are not intended to be limiting unless otherwise specified.

EXAMPLE

These experiments involve the fermentation of a bacterium, *Bacillis subtilis*, and actinomyces, *Streptomyces griseus*, and a fungus, *Tricoderma viride*. *Streptomyces griseus* is grown commercially for the production of antibiotic streptomycin. *B. subtilis* is used commercially as the source of the chemical enzymes used in conjunction with detergents sold for washing clothes, and *Trichoderma viride* is used for converting cellulose to glucose.

The cultivation of the microorganisms was done using a one-liter "Mini-Ferm" fermentor, model M-1000 manufactured by Fermentation Design, Incorporated. The only modifications made to it included the removal of the heater well assembly and the addition of rotameters in the air line to monitor air flow rates. Temperatures was maintained by circulating water from a constant temperature bath through the stainless steel U-tube. It was noted that the temperature never varied more than ± ½ C° during the course of a fermentation.

Air was sterilized by means of fiberglass depth filters, and was metered by Fisher-Porter Tri-Flat rotameters. The air was then sparged into the broth through a fritted glass dispersion tube, Pyrex brand (Corning 39533), coarse porosity, from Arthur H. Thomas Company. The agitation was with two-inch Teflon covered magnetic stirring bars.

For each experimental run, two identical fermentors were used. One fermentor served as a control and the crocetin solution was added to the second fermentor.

Foam was controlled by manually adding equal amounts of sterile anti-foam (Cat. No. 34001, Instrumentation Laboratory, Incorporated) to the fermentors as required.

The *Bacillis subtilis* inoculant was prepared from a fresh shake-flask culture which had been inoculated the previous day from a master agar slant. The *Bascillis subtilis* strain Number 168 was obtained from the Department of Microbiology, University of Virginia. The inoculum to the fermentors was 0.5 ml of the shake flask culture, both fermentors being inoculated from the same syringe.

The broth media used was nutrient broth manufactured by Baltimore Biological Laboratory (BBL). Per liter, it contained 5.0 grams of gelysate$^{tm}$ peptone and 3.0 grams of beef extract. One liter of broth was prepared and well-mixed. Then 500 ml were placed in each of the fermentors just prior to being autoclaved. The fermentor assemblies were autoclaved at 14.5 lb./in$^2$ for 20 min.

After the fermentor assemblies were autoclaved, they were placed on their stands and aerated and agitated overnight to check for contamination. Contamination was detected by noting the turbidity of the broth.

Cell concentrations were obtained by taking 1 ml samples which were then diluted in PBS buffer and plated out on nutrient agar (BBL) plates. PBS buffer is formulated as 8.0 grams of NaCl, 0.2 grams of KCl, 1.15 grams of $Na_2H_2PO_4$, and 0.2 grams of $KH_2PO_4$ per liter of doubly distilled water.

The crocetin salt solution was prepared by dissolving 100 mg of crocetin in 50 ml of 2 normal NaOH, then slowly adding 50 ml of 2 normal HCl until the pH was adjusted to 8.0. Thus, the solution was of a strength of 1 mg of crocetin per ml of solution. The salt of crocetin was used because of its greater solubility in water as compared to the acid form.

The *Streptomyces griseus* inoculant was also prepared in a fresh shake flask culture which had been inoculated the previous day from the master agar slant. The Streptomyces strain used was obtained from the Department of Microbiology at the University of Virginia which had obtained the original culture from the American Type Culture Collection, number 23345. The inoculum to the fermentors was 1 ml of the shake flask culture, both fermentors being inoculated from the same syringe.

The broth medium used for the cultivation of the Streptomyces was a modification of Emerson's broth. Per liter, it contained 5.0 grams of gelysate$^{tm}$ peptone, 3.0 grams of beef extract, 2.5 grams of NaCl and 1 to 5% dextrose depending on the experimental run. After the broth was prepared and well mixed, 750 ml were placed in each of the fermentors just prior to being autoclaved at 14 lb/in$^2$ for 20 minutes.

The cell density was determined by measurement of mycellial dry weight per ml. During the course of the fermentation, 10 ml samples were withdrawn from the fermentor. The samples were then centrifuged, the filtrate removed, washed and centrifuged again. Then the solids were transferred to preweighed aluminum milk pans and dried overnight at 110° C. The pans were then reweighed and the mycellial mass concentration was determined as the difference between the pan weights divided by the sample volume.

The *Trichoderma viride* was obtained from the Department of Biochemistry, Virginia Polytechnic Institute and State University and was also prepared in a shake flask culture which had been inoculated from the master slant. It was then grown in a broth known as Mandel's media, containing solka floc as the source of cellulose (See "Celluloses and Their Applications", Edited by G. J. Hajny and E. T. Reese, Advances in Chemistry Series 95, American Chemical Society, Washington, D.C. 1969).

In all cases, the addition of crocetin to the fermentation broth resulted in increased yields. The *B. subtilis* yields increased from 20–30%, the yields of *Streptomyces griseus* increased by 25–50%, and the yields of cellulose from the *Trichoderma viride* fermentation was increased by 50–60%. No attempt was made to optimize the crocetin concentration used.

Fermentation processes are used to a large extent in industry, at the current time. Many chemicals and drugs are made exclusively by this technique. Obviously, since it is possible to increase fermentation yields, it will also be possible to increase the production rates of these many products, thereby providing a significant advance in the method of preparation of these chemicals and drugs.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method of increasing the yield of a microbial fermentation process which comprises including a water-soluble carotenoid in the nutrient medium for said fermentation process wherein said water-soluble carotenoid has the formula:

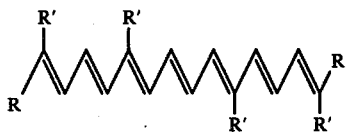

wherein each R is a hydrophilic group and wherein each R' is hydrogen or methyl.

2. The method of claim 1, wherein said water-soluble carotenoid is crocin.
3. The method of claim 1, wherein the water-soluble carotenoid is crocetin, or a salt thereof.
4. The method of claim 3, wherein said fermentation process is the fermentation of *Bacillis subtilis*.
5. The method of claim 3, wherein said fermentation process is for the fermentation of *Streptomyces griseus*.
6. The method of claim 3, wherein said fermentation process is for the fermentation of *Trichoderma viride*.
7. The method of claim 1, wherein the amount of water-soluble carotenoid is from 0.1 to 1000 mg per liter of the fermentation broth.
8. The method of claim 3, wherein the water soluble carotenoid is the sodium salt of crocetin.
9. A fermentation broth which comprises microorganisms, a nutrient medium for fermentation of said microorganism, and an amount of water soluble carotenoid therein effective for increasing the yield of fermentation by said microorganism; wherein said water-soluble carotenoid has the formula:

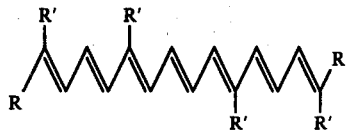

wherein each R is a hydrophilic group and wherein each R' is hydrogen or methyl.

* * * * *